United States Patent
Luyken et al.

(10) Patent No.: US 7,147,757 B2
(45) Date of Patent: Dec. 12, 2006

(54) METHOD FOR SEPARATING AN AZEPINE DERIVATIVE OUT OF A MIXTURE CONTAINING AN AMINE AN AZEPINE DERIVATIVE

(75) Inventors: Hermann Luyken, Ludwigshafen (DE); Frank Ohlbach, Dossenheim (DE)

(73) Assignee: Basf Aktiengesellschaft, Ludwigshafen (DE)

( * ) Notice: Subject to any disclaimer, the term of this patent is extended or adjusted under 35 U.S.C. 154(b) by 455 days.

(21) Appl. No.: 10/204,966

(22) PCT Filed: Mar. 6, 2001

(86) PCT No.: PCT/EP01/02494

§ 371 (c)(1),
(2), (4) Date: Aug. 27, 2002

(87) PCT Pub. No.: WO01/66514

PCT Pub. Date: Sep. 13, 2001

(65) Prior Publication Data

US 2003/0023083 A1 Jan. 30, 2003

(30) Foreign Application Priority Data

Mar. 8, 2000 (DE) ................. 100 10 825

(51) Int. Cl.
*B01D 3/42* (2006.01)
*C07C 255/24* (2006.01)
*C07C 209/82* (2006.01)
*C07D 223/12* (2006.01)

(52) U.S. Cl. ............... 203/2; 203/49; 203/75; 203/77; 203/78; 203/80; 203/DIG. 25; 540/605; 540/612; 558/452; 564/437; 564/497

(58) Field of Classification Search ........... 203/2, 203/49, 73, 78, 80, 28, 77, DIG. 25; 540/605, 540/612, 540; 564/439, 437, 497; 558/452
See application file for complete search history.

(56) References Cited

U.S. PATENT DOCUMENTS

| | | | | | |
|---|---|---|---|---|---|
| 2,208,598 | A | * | 7/1940 | Rigsby | 558/452 |
| 2,762,835 | A | * | 9/1956 | Swerdloff | 558/459 |
| 4,110,326 | A | * | 8/1978 | Tuba et al. | 540/532 |
| 5,192,399 | A | * | 3/1993 | Sieja | 203/36 |
| 5,717,090 | A | * | 2/1998 | Bassler et al. | 540/539 |
| 6,204,408 | B1 | * | 3/2001 | Bassler et al. | 558/452 |
| 6,252,115 | B1 | * | 6/2001 | Luyken et al. | 564/437 |
| 6,300,497 | B1 | * | 10/2001 | Rehfinger et al. | 540/605 |
| 6,649,799 | B1 | * | 11/2003 | Ostgard et al. | 564/385 |

FOREIGN PATENT DOCUMENTS

DE    198 39 338    *    3/2000

* cited by examiner

*Primary Examiner*—Virginia Manoharan
(74) *Attorney, Agent, or Firm*—Novak Druce & Quigg LLP

(57) ABSTRACT

The invention relates to a method for separating by distillation a portion or the entirety of an azeptine derivative (III), which is selected from the group consisting of aminohexylidene imine, tetrahydroazepine, hexylhexahydroazepine and of aminohexylhexahydroazepine, out of a mixture (II) containing an azepine derivative (III) and an amine (I). The inventive method is characterized in that the distillation is carried out with a maximum bottom temperature of 150° C.

7 Claims, No Drawings

METHOD FOR SEPARATING AN AZEPINE DERIVATIVE OUT OF A MIXTURE CONTAINING AN AMINE AN AZEPINE DERIVATIVE

DESCRIPTION

The present invention relates to a process for distillative removal of part or all of an azepine derivative (III) selected from the group consisting of tetrahydroazepine, 2-aminoazepan, N-(2-azepano)-1,6-diaminohexane and N-(2-azepano)-6-aminocapronitrile from a mixture (II) comprising an azepine derivative (III) and an amine (I) selected from the group consisting of 6-aminocapronitrile and hexamethylenediamine, which comprises conducting the distillation at a pot temperature of not more than 120° C.

Mixtures comprising an amine and an azepine derivative are customarily obtained in the hydrogenation of nitriles to amines.

The complete hydrogenation of adiponitrile (ADN) to hexamethylenediamine (HMD), and also the partial hydrogenation with coproduction of HMD and 6-aminocapronitrile (ACN), in the presence of a catalyst based on a metal such as nickel, cobalt, iron, rhodium or ruthenium is commonly known, for example from: K. Weissermel, H.-J. Arpe, Industrielle Organische Chemie, 3rd edition, VCH Verlagsgesellschaft mbH, Weinheim, 1988, page 266, U.S. Pat. Nos. 4,601,859, 2,762,835, 2,208,598, DE-A 848 654, DE-A 954 416, DE-A 42 35 466, U.S. Pat. No. 3,696,153, DE-A 19500222, WO-A-92/21650 and DE-A-19548289.

By-products formed include azepine derivatives such as N-(2-azepano)-1,6-diaminohexane and N-(2-azepano)-6-aminocapronitrile, especially 2-aminoazepan and tetrahydroazepine.

These azepine derivatives, which, because of their color and deleterious effect on product properties, constitute undesirable impurities in the amines, which are customarily used for manufacturing fibers, are difficult to separate from the amines.

For instance, GB-A-893 709 discloses installing a delay time vessel in the reflux line of a distillation column used for purifying HMD.

GB-A-1 238 351 describes the removal of HMD from mixtures comprising HMD and azepine derivatives, by addition of alkali metal hydroxide mixtures.

WO-A-99/48872 discloses distillatively removing azepine derivatives from amines at overhead temperatures of from 160 to 250° C. The disadvantage with this process is unsatisfactory separation.

Disadvantages with the processes mentioned are the use of large vessels, which makes for reduced control of the distillation columns, and the formation of solids, which can lead to blockages, and unsatisfactory removal of the azepine derivatives.

It is an object of the present invention to provide a process for removing an azepine derivative from mixtures comprising an amine and an azepine derivative in a technically simple and economical manner.

We have found that this object is achieved by the process defined at the beginning.

Suitable amines I include aromatic amines such as benzylamine, aliphatic amines such as cyclic amines, for example isophoronediamine, or preferably acyclic amines, for example 1,4-diaminobutane, especially HMD or ACN, and also mixtures thereof.

Such amines can be prepared in a conventional manner.

For instance, HMD can be obtained by partial or complete catalytic hydrogenation with a gas comprising molecular hydrogen, of ADN to HMD or mixtures comprising HMD and ACN.

Catalysts used for this hydrogenation can advantageously be those based on a metal selected from the group consisting of ruthenium, rhodium, nickel, cobalt, preferably iron, in which case the catalysts may include further elements as promoters. In the case of iron-based catalysts, suitable promoters include especially one or more, such as two, three, four or five, elements selected from the group consisting of aluminum, silicon, zirconium, titanium and vanadium.

Such catalysts and the process conditions for the reaction mentioned are described for example in WO-A-96/20166, DE-A-19636768 and DE-A-19646436.

Contemplated azepine derivatives III include especially 2-aminoazepan of the formula

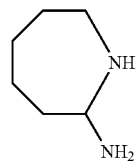

N-(2-azepano)-1,6-diaminohexane of the formula

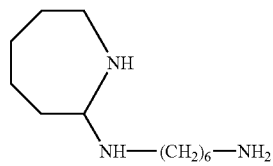

N-(2-azepano)-6-aminocapronitrile

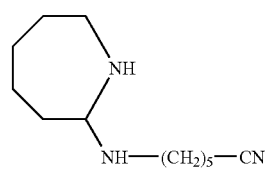

and THA of the formula

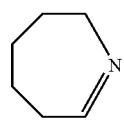

and mixtures thereof.

The azepine derivatives (III) can be present in the mixture (II) as individual compounds or as adducts, for example with an amine (I), in which case these adducts shall for the purposes of the present invention likewise be termed azepine derivatives (III).

Such azepine derivatives and processes for their preparation are commonly known.

For instance, 2-aminoazepan, N-(2-azepano)-1,6-diaminohexane and N-(2-azepano)-6-aminocapronitrile and tetrahydroazepine can generally be obtained in mixtures (II) in amounts from 1 to 10,000 ppm, based on the mixture, in the partial catalytic hydrogenation of ADN with a gas comprising molecular hydrogen to form HMD or mixtures comprising HMD and ACN according to the process described for preparing the amines (I). Similarly, the azepine derivatives mentioned can be formed by oxidation of amines, such as HMD and ACN, for example with gases containing molecular oxygen.

According to the present invention, the distillation is conducted with pot temperatures of not more than 120° C., preferably not more than 110° C. The distillation is advantageously carried out at pot temperatures of not less than 50° C., preferably not less than 80° C.

The distillation can be carried out continuously.

The distillation can be carried out batchwise.

When HMD is used as amine (I) and one or more compounds selected from the group consisting of AHI, HHA, AHHA and THA as azepine derivative (III), then the distillation pressure, as measured at the bottom of the distillation apparatus, should be within the range from 1 to 300 mbar, preferably within the range from 5 to 100 mbar, especially within the range from 10 to 60 mbar.

When ACN is used as amine (I) and one or more compounds selected from the group consisting of 2-aminoazepan, N-(2-azepano)-1,6-diaminohexane and N-(2-azepano)-6-aminocapronitrile and tetrahydroazepine as azepine derivative (III), then the distillation pressure, as measured at the bottom of the distillation apparatus, should be within the range from 1 to 200 mbar, preferably within the range from 5 to 100 mbar, especially within the range from 10 to 40 mbar.

Advantageously, amine (I) is obtained above the feed of mixture (II) to the distillation apparatus, especially at the top of the distillation apparatus.

Advantageously the distillation provides a bottom product (VI) having a higher weight fraction of azepine derivative (III) than mixture (II).

Suitable apparatus for the distillation is any customary distillation apparatus as described for example in Kirk-Othmer, Encyclopedia of Chemical Technology, 3rd Ed., Vol. 7, John Wiley & Sons, New York, 1979, pages 870–881, such as sieve plate columns, bubble cap columns or columns packed with arranged or dumped packing.

The distillation can be carried out in a plurality of columns, such as 2 or 3, but is advantageously carried out in a single column.

In a preferred embodiment, the distillation can be carried out in two stages.

The first stage can consist of a plurality of columns, such as 2 or 3, advantageously a single column. The second stage can consist of a plurality of columns, such as 2 or 3, advantageously a single column.

Advantageously the pressure in the first stage, measured in the pot, is at least 1.5 times, especially at least double, the pressure in the second stage, measured in the pot.

Advantageously not less than 20% by weight of the amount fed into the first stage per unit time is removed from the pot of the first stage and fed to the second stage.

Advantageously the overhead product of the second stage can be recycled into the first stage.

Advantageously the distillation mixture has added to it a compound (IV) whose boiling point is above that of said amine (I) under the distillation conditions. Compounds (V) useful for this purpose are in particular compounds (V) that are inert to the amine (I) under the distillation conditions.

Useful compounds (IV) include compounds from the group consisting of aromatics, aliphatics, such as cyclic and acyclic aliphatics, and aliphatic-aromatic compounds. These compounds may bear substituents, such as a hydroxyl, keto, ester, alkyl, aryl, cycloalkyl, arylalkyl group, preferably a nitrile or amino group, or a plurality of identical or different such groups.

Said compound (IV) can be a single compound or a mixture of such compounds.

Advantageous compounds (IV) are convertible in a simple manner, as by catalytic hydrogenation with a gas containing molecular hydrogen, for example, into a mixture (V) comprising an amine (I) and an amine (III) or in particular a mixture (II).

The products obtained in this conversion can be advantageously reused in the process of the invention.

The difference in the boiling points between the amine (I) and the compound (IV) should be from 1 to 200° C., preferably from 5 to 100° C., under the distillation conditions.

The compound (IV) can be added to the mixture (II) before or during the distillation.

The addition of the compound (IV) to the mixture (II) before the distillation can be carried out in the conventional manner in customary mixing apparatuses. With this procedure, the addition of a mixture of mixture (II) and compound (IV) into the distillation apparatus is contemplated.

The addition of the compound (IV) to the mixture (II) during the distillation can be effected by feeding the compound (IV) into the distillation apparatus preferably in the bottom region.

The distillation can advantageously be carried out in the presence of assistants which support the distillative separation of the invention, especially in the presence of carbon dioxide.

The concentration of azepine derivative (III) in the pot, based on the mixture present in the pot, is not more than 0.5% by weight, preferably not more than 0.2% by weight, especially not more than 0.15% by weight, during the distillation.

The process of the invention customarily affords the predominant proportion of azepine derivative (III) as bottom product (VI). This bottom product (VI) customarily includes azepine (III) in a higher weight concentration than the mixture (II) used for distillation according to the process of the invention (II).

Bottom product (VI) can advantageously be subjected in a conventional manner, for example according to the processes already mentioned for preparing HMD or mixtures comprising HMD and ACN, to a catalytic hydrogenation to obtain an amine (I), such as HMD or mixtures comprising HMD and ACN. In the hydrogenation, azepine derivative (III) can be converted into organic compounds, such as hexamethylimine, which mixed with amine (I) permit removal of amine (I) in a technically simple and economical manner.

HMD and ACN are intermediates for industrially important polyamides, such as nylon-6 or nylon-6,6.

EXAMPLES

Percentages are by weight, unless otherwise stated.
THA is tetrahydroazepine.
The product mixtures were analyzed by gas chromatography. THA concentrations below 20 ppm were determined by polarography.

Inventive Example 50 kg/h of HMD having a THA content of 71 ppm were fed at a uniform rate to a distillation column having 50 theoretical plates and 41 kg/h of overhead product and 9 kg/h of bottom product were removed from the distillation apparatus at a reflux ratio of 1, a base-of-column pressure of 73 mbar and a pot temperature of 119.9° C.

The overhead product as well as HMD included 12 ppm of THA, the bottom product 334 ppm of THA.

Comparative Example

The inventive example was repeated except that the base-of-column pressure was 255 mbar and the pot temperature 153.5° C. The overhead product as well as HMD included 44 ppm of THA, the bottom product 172 ppm of THA.

We claim:

1. A process for distillative removal of part or all of an azepine derivative (III) selected from the group consisting of tetrahydroazepine, 2-aminoazepan, N-(2-azepano)-1,6-diaminohexane and N-(2-azepano)-6-aminocapronitrile from a mixture (II) comprising an azepine derivative (III) and an amine (I), which comprises conducting the distillation at a pot temperature of not more than 120° C., and wherein the distillation provides said azepine derivative (III) predominantly as bottom product (VI) and said bottom product (VI) is subjected to a hydrogenation.

2. A process as claimed in claim 1, wherein said bottom product (VI) is used in a hydrogenation to prepare an amine (I).

3. The process of claim 1, wherein the amine (I) is 6-aminocapronitrile or hexamethylenediamine.

4. A process for distillative removal of part or all of an azepine derivative (III) selected from the group consisting of tetrahydroazepine, 2-aminoazepan, N-(2-azepano)-1,6-diaminohexane and N-(2-azepano)-6-aminocapronitrile from a mixture (II) comprising an azepine derivative (III) and an amine (I), which comprises conducting the distillation at a pot temperature of not more than 120° C., and wherein the distillation is carried out in two stages, the pressure in the first stage, measured in the pot, is at least 1.5 times the pressure in the second stage, measured in the pot, not less than 20% by weight of the amount fed into the first stage per unit time is removed from the pot of the first stage and fed to the second stage; and the overhead product of the second stage is recycled into the first stage.

5. The process of claim 4, wherein the amine (I) is 6-aminocapronitrile or hexamethylenediamine.

6. A process of distillative removal, of part or all of an azepine derivative (III) selected from the group consisting of tetrahydroazepine, 2-aminoazepan, N-(2-azepano)-1,6-diaminohexane and N-(2-azepano)-6-aminocapronitrile from a mixture (II) comprising an azepine derivative (III) and an amine (I), which comprises conducting the distillation at a pot temperature of not more than 120° C.,and wherein the distillation is carried out in the presence of carbon dioxide.

7. The process of claim 6, wherein the amine (I) is 6-aminocapronitrile or hexamethylenediamine.

\* \* \* \* \*